United States Patent
Schawaller et al.

(10) Patent No.: US 7,205,155 B1
(45) Date of Patent: Apr. 17, 2007

(54) METHOD FOR THE DETERMINATION OF SUBSTANCES USING THE EVANESCENCE FIELD METHOD

(75) Inventors: Manfred Schawaller, Cressier (CH); Gerald Quapil, Owen/Teck (DE)

(73) Assignees: Stiftung fur Diagnostische Forschung, Cressier sur Morat (CH); Leuze Electronic GmbH & Co, Owen/Teck (DE)

( * ) Notice: Subject to any disclaimer, the term of this patent is extended or adjusted under 35 U.S.C. 154(b) by 697 days.

(21) Appl. No.: 10/049,975

(22) PCT Filed: Aug. 18, 2000

(86) PCT No.: PCT/EP00/08116
§ 371 (c)(1), (2), (4) Date: Oct. 1, 2002

(87) PCT Pub. No.: WO01/14859
PCT Pub. Date: Mar. 1, 2001

(30) Foreign Application Priority Data
Aug. 20, 1999 (EP) .................................. 99116418

(51) Int. Cl.
*G01N 33/543* (2006.01)
*G01N 33/569* (2006.01)

(52) U.S. Cl. .................... 436/172; 435/5; 435/7.32; 435/7.5; 436/164; 436/518; 436/524; 436/527; 436/800; 436/805; 436/815; 436/817

(58) Field of Classification Search ................... None
See application file for complete search history.

(56) References Cited

U.S. PATENT DOCUMENTS

| | | | |
|---|---|---|---|
| 4,444,879 A * | 4/1984 | Foster et al. ................ | 435/7.95 |
| 4,451,434 A | 5/1984 | Hart | |
| 5,300,423 A | 4/1994 | Zoha et al. | |

FOREIGN PATENT DOCUMENTS

WO    WO 96/09532 A    3/1996

* cited by examiner

*Primary Examiner*—Christopher L. Chin
(74) *Attorney, Agent, or Firm*—Weingarten, Schurgin, Gagnebin & Lebovici LLP

(57) ABSTRACT

This invention relates to a method for the determination of substances using the evanescence field method. A cuvette, a microtiter well, a solution and a kit for application in a method according to the invention are disclosed. This method can in particular be used in the field of diagnostics and in analytical procedures.

29 Claims, 6 Drawing Sheets

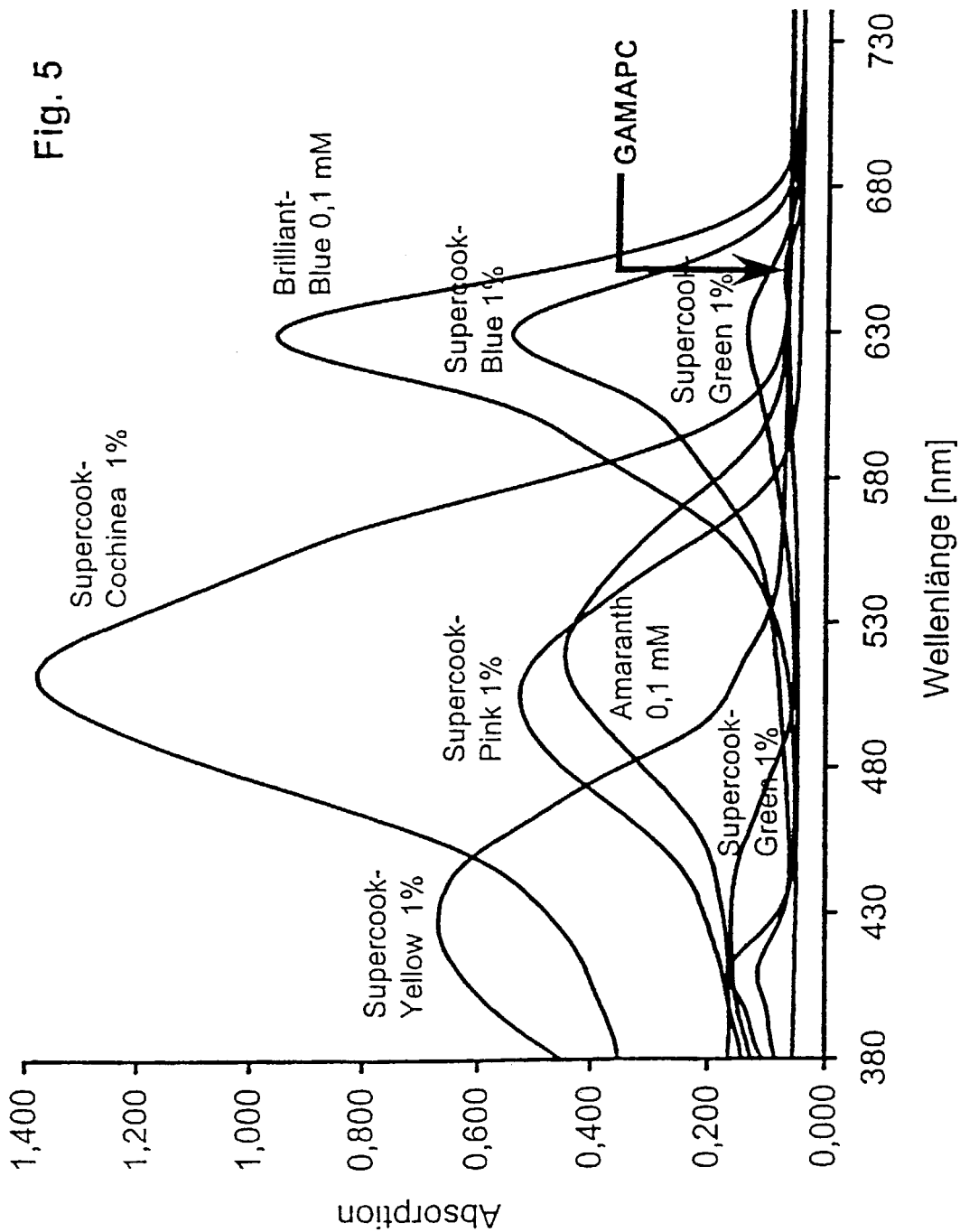

METHOD FOR THE DETERMINATION OF SUBSTANCES USING THE EVANESCENCE FIELD METHOD

DESCRIPTION

The present invention concerns a method for assaying substances based on the evanescence field method and a cuvette, a microtiter plate, a solution and a kit for use with the method in the invention. This invention can be used particularly in diagnosis and analysis.

Medical diagnostics, especially immunological diagnostics, is largely based on the ELISA (Enzyme-Linked-Immunoabsorbent Assay). A recent review of immune assays can be found in Hage, Anal. Chem. 71 (1999), 294R–304R. An ELISA test is used to determine the concentration of antigens or antibodies. The substance being studied (for example, an antigen) is first placed in contact with a solid substrate to which a specific reaction partner for the substance being studied is first coupled (for example, an antibody). By binding the substance being studied to the reaction partner coupled to the substrate, the substance being studied is concentrated on the solid substrate. Then, a second reaction partner (for example, another antibody) for the substance being studied is placed in contact with the substrate, and this reaction partner is marked with an enzyme, which allows colorimetric detection. When this second reaction partner reacts with the substance being studied coupled to the surface of the substrate, a colored product is produced that can be evaluated optically. Standardized plastic plates, frequently made of polystyrene, with 96 wells are mostly used as the solid phase. The surface of the plastic wells binds proteins in the nanogram range through absorption in a quantity sufficient for immunological detection. There are several ways of marking the second reaction partner, which is mostly an immunoglobulin, with an enzyme. Markers currently used are peroxidase or alkaline phosphatase.

ELISAs give very good results in terms of sensitivity and specificity, and the detection limits that can be reached are in the nanogram range or below it. There is a wide variety of embodiments of assays that are based on this principle. With it, antigens or antibodies can be detected, depending on what the question is.

However, a major disadvantage of the ELISA is handling the test, since different reagents are added to the wells one after another and must be removed again. Ten or more pipetting, washing and incubation steps in all may be necessary. So ELISAs are very time-consuming and labor-intensive, and must be done by specially trained personnel with great care. Another disadvantage of the ELISA is the time it takes for all the incubation and washing steps for an assay or test, which normally lasts one hour or more.

With the evanescence field method, the interaction of biomolecules, for example, on a surface can be observed directly. Here, the interaction of reactants in solution is measured with a solid matrix surface. It is possible to measure the binding of the ligands physically as "surface plasmon resonance" in "real time."

The advantages compared to an ELISA are the elimination of other pipetting steps after the addition of the reagents and the elimination of the waiting steps. In the past, expensive apparatuses and multi-layer sensor chips with special surface chemistry were needed for such measurements. These disadvantages prevent the method from being used in routine diagnostics.

Thus, the technical problem underlying the present invention is based on providing a method of assaying substances, especially biologically active substances in which the washing and pipetting steps usual with an ELISA can be avoided as much as possible, and the incubation times can be reduced. This method should also require inexpensive sensor chips and cuvettes that are easy to produce and available.

The embodiments in the claims provide a solution to the above technical problem.

In particular, the invention provides a method of assaying substances that has the following steps:

providing a surface that has at least one reaction partner R1 for a reaction partner R2 bonded to the surface, placing in contact with the surface a solution that contains at least the substance being assayed, at least one compound containing fluorophor and at least one dye that absorbs in the absorption and/or emissions range of the fluorophor, wherein a complex forms at reaction partner R1 on the surface by means of reaction partner R2 and wherein that complex includes, besides reaction partner R1 at least the substance being studied and the compound containing at least one fluorophor, and exciting the fluorophor bonded to the surface by the evanescence field of a light source and measuring the fluorescence produced.

The figures show:

FIG. 5 shows the absorption spectra of a series of dyes.

Figure 1:
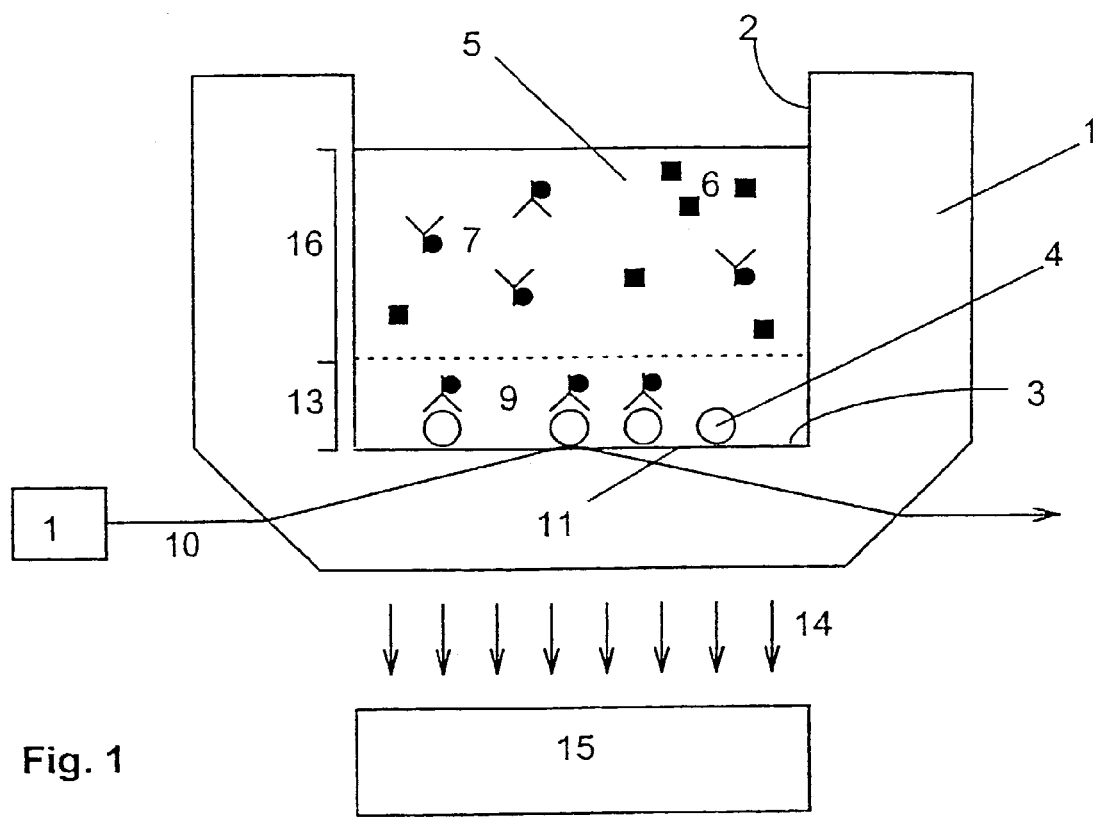
FIG. 1 is a schematic view of an embodiment of the cuvette in the invention and the method in the invention in one form of embodiment.

However, the surface in this comparative example was not coated with reaction partner R1 for the protein.

According to the invention, first a surface is prepared that has at least one reaction partner R1 bonded or immobilized. Bonded preferably means that the reaction partner R1 is adhered to the surface by absorption (direct absorption). But the reaction partner R1 can also be bonded to the surface via a bridge element, for example a protein, such as an antibody or an antigen. The reaction partner R1 can also be bonded to the surface by a covalent bond. This can be produced with an acrylate surface by conversion with a carbodi-imide, for example. The term "bonded" in the sense of the invention means adhesion of a reaction partner or connection to a surface or to another reaction partner and/or connection, and includes both covalent and non-covalent interactions, like for example interactions based on ionic, polar or non-polar interactions.

Reaction partner R1 can be placed on the surface by a common method. For example, a protein serving as reaction partner R1 can be coated on the surface. Reaction partner R1 can preferably be bonded to the surface by absorption or by a covalent bond. After this step, the surface is preferably treated with another solution, and places on the surface not adhered to reaction partner R1 are blocked or will be blocked, for example by another protein that basically does not react with the components contained in the solution to make contact. The above surface is the inside of a concave container, like a cuvette or a well of a microtiter plate, for example.

According to the invention, reaction partner R1 bonded to the surface can form a complex by means of reaction partner R2 on the surface, whereby this complex includes, besides reaction partner R1, at least the substance being assayed and the component containing at least one fluorophor. With reaction partner R1 bonded to the surface, the complex with the substance being assayed is "anchored" to the surface, i.e., fixed and can at the same time be detected by marking it with a compound containing the fluorophor.

According to the invention, a "complex" or "conjugate" is understood to be a molecular coupling or bonding between two or more preferably chemical or biochemical substances. The complex is preferably formed by means of selective and/or specific conversions, especially preferred by antigen-antibody reactions. According to the invention, the term "conversion" includes both covalent and non-covalent interactions of two or more reaction partners, wherein both types of interaction can take place one after another within a complex or conjugate. Non-covalent interaction can mean, for example, Van der Walls interactions, polar and/or ionic interaction of reaction partners. The term "reaction partner" means a compound with an affinity for another substance in this invention.

According to the invention, the complex includes, besides reaction partner R1, at least the substance being assayed and the compound containing at least one fluorophor.

The following are ways, inter alia, of binding this complex to reaction partner R1 by means of reaction partner R2.
(1) The substance being assayed is itself reaction partner R2.
(2) The substance being assayed contains reaction partner R2, i.e., reaction partner R2 is a part of the structure of the substance being assayed.
(3) The substance being assayed has an affinity or binding site for reaction partner R2. After reaction partner R1 is bonded to the substance being assayed, case (2) can therefore apply.
(4) Another compound contains reaction partner R2 or has an affinity for reaction partner R2, whereby this other compound also contains at least one binding site for the substance being assayed. In this case, the other compound, the substance being assayed and the reaction partner R2 can be in the solution as a conjugate or complex (all or only individually) or the conjugate is formed in the solution.

Preferred embodiments of these cases (1) to (4) will be described in greater detail below.

In one preferred embodiment of the method in the invention, the substance being assayed can itself have an affinity for reaction partner R1 on the surface and can therefore bind directly with that reaction partner R1. In this embodiment, the substance being assayed, as reaction partner R2, can bind to reaction partner R1 on the surface. When the substance being assayed is an antibody, for example, an antigen specific for that antibody can be placed on the surface, or vice versa.

FIG. 1 shows a schematic view of an embodiment of the cuvette in the invention, and the method in the invention according to the embodiment above. The cuvette 1 has a well 2, whose surface 3 contains reaction partner R1 4 bonded for the protein being assayed. The well 2 also holds the solution 5 to be placed in contact with the surface 3, which, in this embodiment, is a dye 6 and the substance 7 being assayed, which already exists as a conjugate with the compound containing fluorophor. The substance being assayed reacts with reaction partner R1 bonded to the surface into a complex 9 on the surface 3. For example, with a laser diode 12, a beam of light 10 is projected onto the bottom of the surface 3, which is totally reflected on the surface of the phase boundary 11. That way, an evanescence field 13 is formed over the surface 3 in which there is basically only fluorophor bonded to the surface in complex 9. In contrast to the schematic view in FIG. 1, the evanescence field usually does not extend over the whole width of the base of the cuvette. For example, the evanescence field can an expansion of roughly 1 $mm^2$. By exciting the fluorophor through the evanescence field 13, the fluorophors bonded to the surface emit photons 14, which can be enhanced by means of a photomultiplier 15, for example, and can be measured. The fluorescence of the volume 16 is basically suppressed by the presence of the dye 6.

In another preferred embodiment, the substance being assayed itself has (basically) no affinity or only a small affinity for reaction partner R1 on the surface. In this case, the solution to be placed in contact with the surface contains, for example, another compound that contains reaction partner R2 and a binding site for the substance being assayed. Reactions partner R2 can bind to reaction partner R1 on the surface and thus fixes the substance being assayed indirectly to the surface. This other connection serves as a bridge element between the substance being assayed and reaction partner R1 on the surface. For example, avidin can be present as reaction partner R1 on the surface. The other compound then contains, besides a binding site for the substance being assayed, for example biotin, which can bind to the avidin bonded to the surface. This embodiment has the advantage that a surface coated with avidin, unlike many antibodies and antigens, can be lyophilized and dried or is very stable lyophilized. In addition, the avidi/biotin system has a very high dissociation constant $K_D$. It is also possible for a series of different assays to be done on a surface coated with avidin and to assay only the other compound, which is placed in contact with the surface with the solution, on the substance being assayed.

Figure 2:
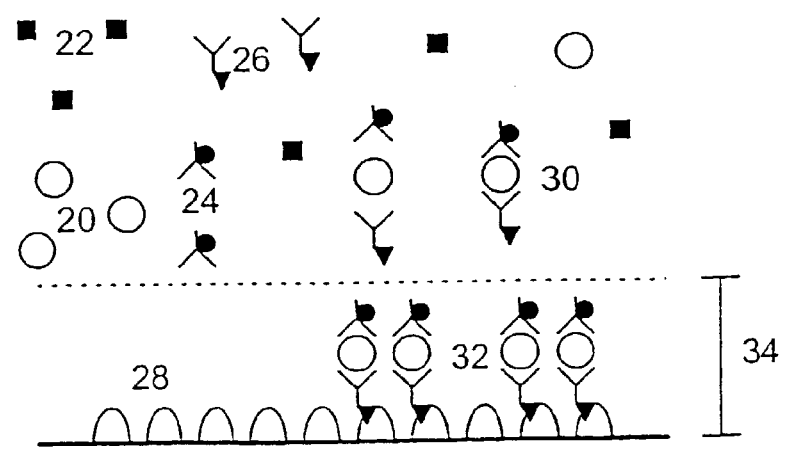
FIG. 2 shows a schematic view of another embodiment of the method in the invention.

FIG. 2 shows this embodiment of the method in the invention schematically. In the solution placed in contact with the surface are, next to one another, the substance being assayed 20, a dye 22, a compound 24 containing fluorophor and another compound 26. Reaction partner R1 28 is bonded to the surface. The other compound and the compound containing fluorophor are absorbed on the substance being assayed (conjugate 30), and the conjugate 30 is bonded via reaction partner R2 present in the other compound 26 on reaction partner R1 28 on the surface to complex 32. Thus, complex 32, which includes compound 24 containing fluorophor, is bonded to the surface and can be assayed by measuring the fluorescence in the evanescence field 34.

For this embodiment of the method of the invention, besides the avidin (or streptavidin)/biotin system, all ligands or ligand-binding systems in which proteins, for example, have selective and/or specific binding sites for one or more ligands, like for example histidine, histidine tags, lectin and/or digoxigernin, and naturally antigen/antibody systems are suitable.

The solution in the invention that is placed in contact with the surface also contains at least one compound containing fluorophor. According to the invention, a fluorophor is understood as a fluorescing compound, such as a fluorescent dye. Fluorescing proteins and/or low-molecular fluorescing chemical compounds are preferred. According to the invention, phycobili proteins, such as Allophycocyanine (APC), Cryptofluor Crimson or Cryptofluor Red can be used as fluorescing proteins. Cy5 or BODIPY (4,4-diluor-4-bora-3a, 4a-diaza-s-indazene-fluorophore) [sic] can be cited as examples of low-molecular fluorescing compounds. Fluorescing dyes with an absorption range from 600 to 700 nm are preferred.

Instead of a fluorophor, a fluorophor precursor compound can be used, from which the fluorophor is released before the measurement process, for example, by changing the pH value or by splitting a protective group.

According to the invention, the term fluorophor also includes phosphorescing compounds. If such a phosphorescing compound is used as a fluorophor, the phosphorescence radiated, which is staggered in time from the excitation, is determined. Thus, it is possible to separate the radiation time from the measurement time.

This compound containing fluorophor also has a binding site for the substance being assayed. For example, the fluorophor can come bonded to an antibody. This antibody containing fluorophor can preferably react as an antigen in an antigen-antibody reaction with the substance being assayed, for example a protein.

In another embodiment, the substance being assayed itself comes as a compound containing fluorophor. In this embodiment, competitive assays are done, which are characterized especially by a low detection limit.

With the method in the invention, a wide variety of substances can be detected. The method is especially suitable for assaying biologically active substances, like hormones, proteins like antigens, antibodies or haptenes, pharmaceuticals, viruses, bacteria, etc. But the method can also be used to detect environmental poisons, toxins, etc.

It is especially preferred for the substances being assayed to be detected by immunologic reactions.

According to the invention, a complex is formed of at least the first reaction partner R1, the substance being assayed and the compound containing fluorophor on the surface. Then, it is possible to measure the fluorophor bonded to the surface by exciting the evanescence field of a light source and measuring the fluorescence of the fluorophor.

When exciting the fluorophor bonded to the surface with an evanescence field, a beam of light is pointed at the bottom of the surface at an angle such that total reflection occurs at the cuvette/solution phase boundary. This forms an evanescence field above the surface in the solution, which can penetrate up to several hundred nanometers into the fluid. According to this invention, an angle of incidence of at least 60° to 90° is preferred, so that an evanescence field at a height up to 400 nm, preferably 200 nm, and especially preferred 50 to 150 nm, is formed over the surface. Within this evanescence field, the beamed light may excite suitable fluorophors. The fluorescent light emitted is enhanced with a photomultiplier, for example, and evaluated.

Since only the fluorophor bonded to the surface is in the evanescence field, only this bonded fluorophor is optimally excited and emits photons. A compound that contains fluorophor and is not bound in the solution is not in the area of the evanescence field, is therefore basically not excited and also basically emits no photons. This arrangement thus allows quantitative determination of fluorophor bonded to the surface in the presence of fluorophor in the supernatant solution without a prior separation and/or washing step.

Monochromatic light can be used as the light source. Light should be used that has a wavelength that preferably does not interfere with the emission of the fluorophor and preferably intersects with the absorption band of the dye. A laser is especially preferred as a light source, whose light emits a wavelength of at least 635 nm. In particular, if the supernatant solution is a serum, lasers that emit wavelengths from 600 to 700 nm are preferred, since the serum's inherent fluorescence is roughly 580 nm.

In one embodiment of the invention, the addition of the fluorophor bonded to the surface can be measured directly (in real time) with a time-progressive reaction. Since the quantity of fluorophor bonded to the surface is directly proportional to the original amount of compound containing fluorophor, the method in the invention makes it possible to make a quantitative determination of reactants found in the solution in real time without other additional washing and/or pipetting steps.

Since the absorption coefficients and the emission properties of fluorophors are very good, the detection limits are small. After only a few minutes, reactions can be assessed qualitatively and/or quantitatively.

However, the scatter of the light beam in the cuvette, which is not ideal, poses a problem, even if physical measures are taken to reduce the scatter light. Due to scatter, light also gets into the volume in the cuvette and causes background fluorescence there. The term "volume" is understood in the present invention to be the liquid outside the evanescence field, which contains unbonded compounds containing fluorophor. The polarization of the light beam can also be turned in both plastic and glass cuvette. This leads, in particular, to reflections of the excitation light during uncoupling, creating so-called vagabond light, which, along with volume and surface scatter effects, can result in excitation of the volume.

According to the invention, excitation of the fluorophor in the volume can be suppressed if the solution to be placed in contact with the surface has at least one dye added to it that has an absorption in the absorption and/or emissions range of the fluorophor.

A comparison of the penetration depth of evanescent waves and vagabond light shows that suppressing volume excitation by adding a dye works. Physically, the light absorption is described by Lambert-Beer's Law, whereby the intensity of the light decreases logarithmically with the distance due to absorption:

$$I[x] = I_o \mathrm{Exp}(-\alpha cx)$$

Figure 3:
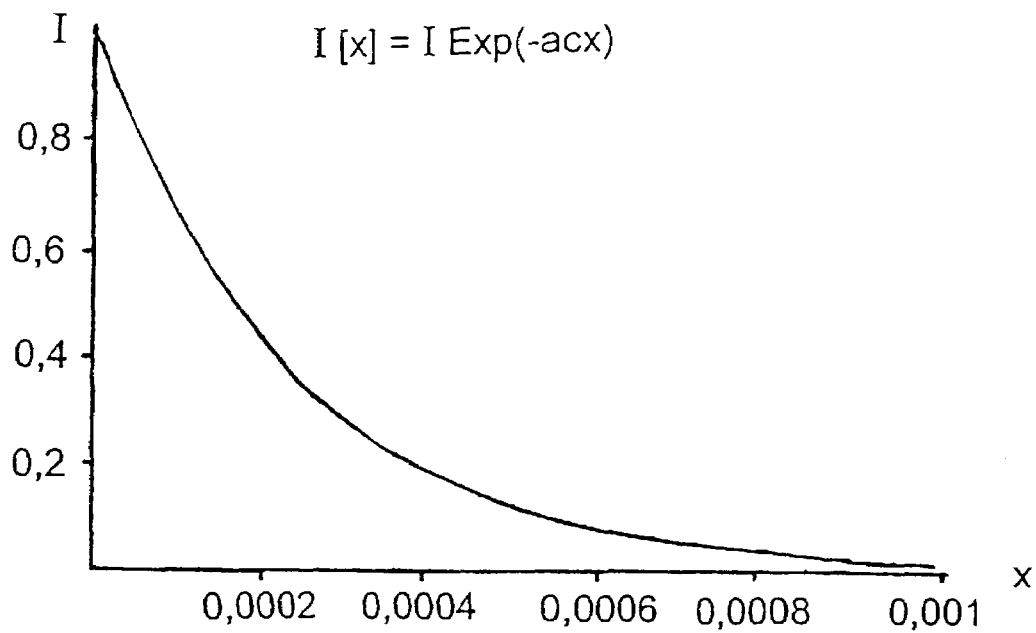
FIG. 3 shows changes in the intensity of electromagnetic radiation in a dye solution according to Lambert-Beer's Law.

Whereby $I_o$ is the intensity of the light shining into the absorbing medium, I is the intensity of the light coming out of the absorbent medium, x is the thickness of the absorbing medium (layer thickness), $\alpha$ is the absorption coefficient and c the concentration of a dye in the solution. FIG. 3 gives the changes in the intensity of a solution of an absorber dye with increasing layer thickness, showing the change in intensity for $\alpha = 100,000$ Mol/(l×cm) and c=20 mMol up to a depth of 1 mm. It must be recognized that over this distance, the scatter light is weakened to 1/100 of its initial intensity. Since the scatter light is predominantly coupled laterally, this weakening is enough to keep the volume signal and hence also the measurement uncertainty for the time-dependent signal of the reaction kinetics, on which this signal to overlapped, within practical usable limits.

Figure 4:
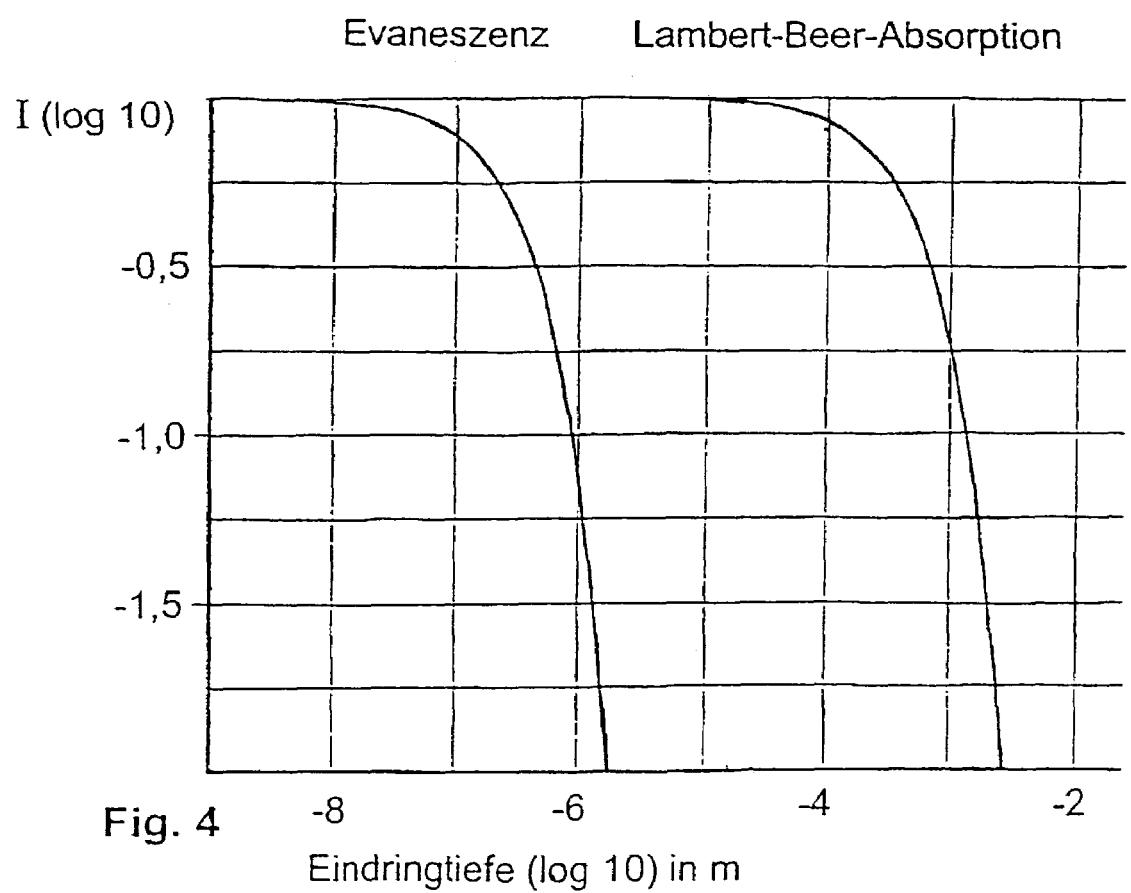
FIG. 4 shows a double logarithmic view of changes in the intensity as a function of the penetration depth of an evanescent wave and a wave weakened by absorption according to Lambert-Beer's Law.

FIG. 4 shows a comparison of the penetration depths for the evanescent wave with the penetration depth of the light during absorption by a dye. This double logarithmic view shows the changes in intensity depending on the penetration depth of an evanescent wave (left) and a wave weakened by absorption (right). The ordinate is in the range from −2 to 0, i.e., from 1/100 to 1 log 10 intensity. The parameters on which it is based are technically feasible values. Although damping the vagabond light permits much greater penetration depths than the light of the evanescent wave, volume excitation and/or emission can still be suppressed efficiently and basically quantitatively, as will be shown in the examples.

The decisive factor for the efficacy of the suppression is the geometric distance between that part of the surface of the cuvette from which light can reach the detector, and the penetration sites of the vagabond light in the volume.

As is clear from FIG. 4, a distance in the range of one millimeter is enough to weaken scatter light of two magnitudes. This distance can be maintained simply by corresponding dimensioning of the cuvette.

The absorption of the dye added to the volume is coordinated with the absorption and/or emission range of the fluorophor in the invention. One individual dye or a mixture of dyes can be used. The absorption range of the fluorophor generally correlates with the wavelength of the light source used. It is not necessary that the dye have an absorption maximum in this special range; a shoulder in the absorption spectrum can suffice. For example, if fluorophors like APC or Cy5 are used, the dye used can have an absorption between 600 nm and 700 nm, like for example Brilliant Blue FCF. The concentration of dye added depends on both the absorption coefficient of each dye in solution and the frequency of the light radiated. The concentration of dye can be adjusted, depending on the dye, so that the penetrating light can basically be absorbed within 1 mm above the surface. To determine the optimal concentration of dye, first the volume fluorescence and the fluorescence in the evanescence field, i.e., the surface fluorescence, are measured for various concentrations of dye (see FIG. 6a). Then, the ratio of the surface fluorescence to volume fluorescence is plotted against the concentration of dye (see FIG. 6b). The maximum of curve 6b represents the optimum concentration of dye. According to the invention, "signal/noise ratio" is the ratio of surface fluorescence (signal) to volume fluorescence ("noise"). "Basically absorbed" can mean an intensity cancellation of 70%, preferably 80% and especially preferred at least 90%.

For example, when Brilliant Blue FCF is used as the dye, a concentration of 0.04 mM is enough to suppress far more than 95% of the volume fluorescence (see Table 4, Example 4). Since the necessary concentration of dye depends, inter alia, on the cuvette used, the measurement layout, etc., even smaller dye concentrations may suffice for an adequate signal/noise ratio. For example, the concentration of Brilliant Blue FCF is preferably at least 0.001 mM.

Figure 6B:
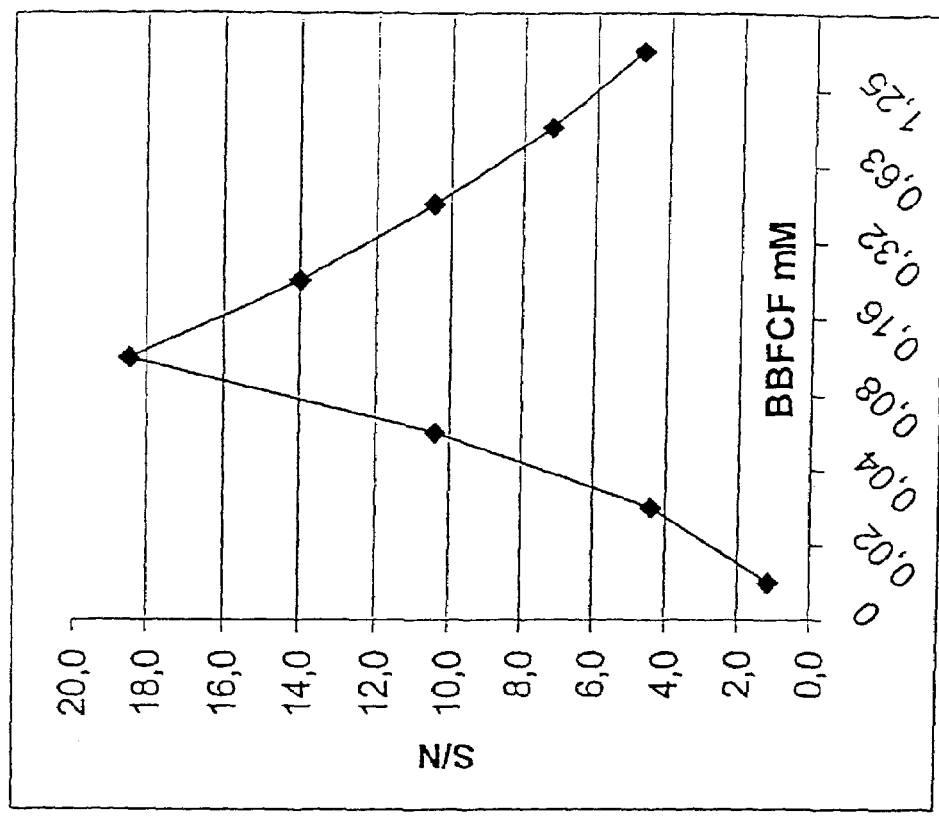
FIG. 6 shows the determination of the optimum concentration of a dye for use in the method in the invention.
Figure 6A:
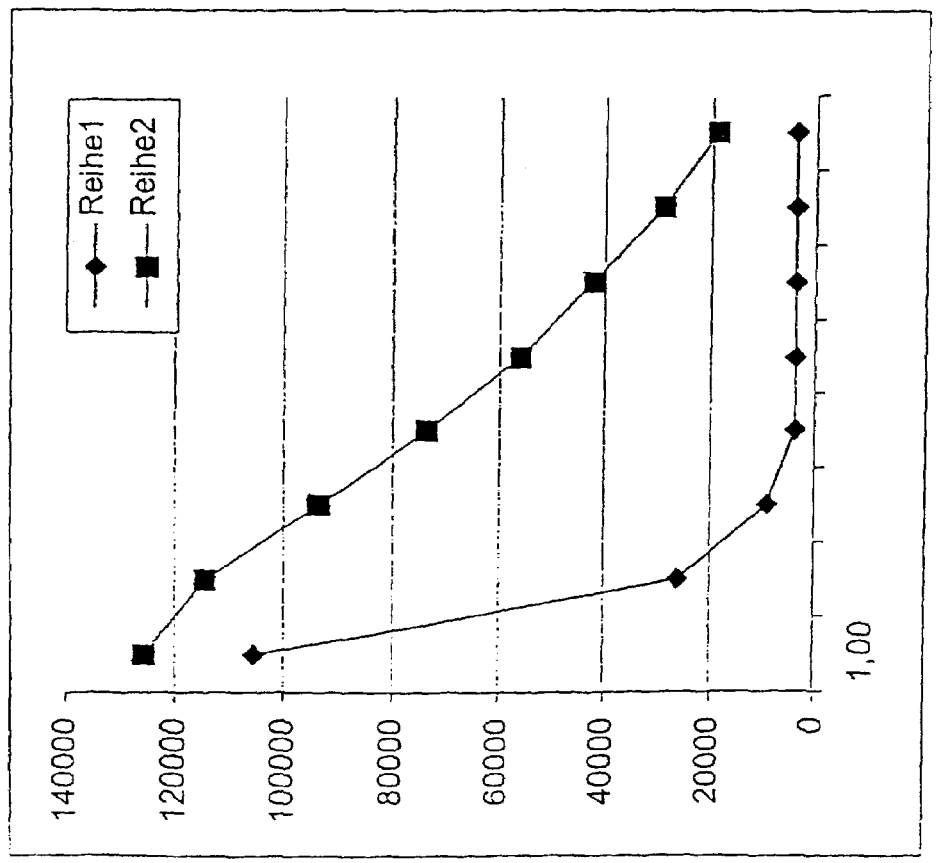

Comparative experiments, as shown in FIG. 6a and 6b, have shown that the signal/noise ratio of 1.3:1 to up to 18.5:1 could be improved with the method in the invention.

The present invention also relates to a cuvette and a microtiter plate for the method in the invention. The cuvette preferably contains glass or a plastic, especially preferably a plastic, such as polystyrene, polypropylene, polyethylene, polyethylene terephthalate, polycycloolefin, polyacrylnitrile, polymethylmethacrylate and/or mixtures are blends of these plastics. In principle, any plastic that basically absorbs no light in the visible range is suitable. In one form of embodiment, the plastic can also be dyed light blue, for example, in order to filter out an emission caused by scatter light. Plastic cuvettes can be obtained inexpensively by injection molding and preferably have a reaction volume of 1 to 400 µl, and especially preferred 5 to 200 µl. Preferably, the cuvettes or microtiter plates in the invention are made in one piece. It can also be an advantage if the inside and/or emission surface, i.e., the surface from which the emitted beam comes out of the cuvette, is/are polished to a surface roughness of preferably 10 nm maximum.

The small dimension and low price make using the method in the invention feasible in routine diagnostics and analysis. In practical application, this type of cuvette or microtiter plate can be pre-prepared and sold commercially closed with a special label. The pre-preparation includes coating the surface of the cuvette or microtiter plate with the first reaction partner and, if necessary, then blocking the uncoated places. It is especially preferred if the coated cuvette or microtiter plate comes lyophilized or dried. The compound containing at least one dye and/or at least one fluorophor and/or the other compound can come lyophilized and/or dried in a closed cuvette or microtiter plate, so that the substance being studied need only be added to the solution. Providing the cuvette or microtiter plate with a serial number makes it possible to have clear attribution of the manufacturing lot, the detection reaction and the sample at any time.

This invention also includes a solution that contains at least one compound a fluorophor, and/or at least one dye that absorbs in the absorption and/or emissions range of the fluorophor. The solution in the invention can also contain another compound that has at least one binding site for the substance being assayed and which includes reaction partner R2.

The invention also includes a kit, which can contain a cuvette or microtiter plate pre-prepared as described above, and/or solutions of at least one dye and at least one compound containing a fluorophor and, if necessary, another compound that has at least one binding site for the substance being assayed and reaction partner R2. The compound containing at least one dye and at least one fluorophor can come together in one solution and in two separate solutions.

This invention also relates to the use of the method in the invention for determining reaction kinetics, preferably immunologic reactions, as well as the use of the method in method or veterinary medical diagnostics, food analysis, environmental analysis or analysis of fermentation processes.

Examples of specific applications that can be cited are detection of plant protection media, such as atrazine, in drinking water, detection of hormones in veal, detection of hormones like HCG and direct or indirect detection of viruses, such as Hepatitis S and HIV.

The invention will be further explained with reference to the examples below.

EXAMPLE 1

In this example, the influence of the concentration of the fluorophor bonded to a protein and added is determined. In this measurement, the only fluorophor is the one bonded to the surface; unbonded fluorophor was washed away. A dye was not added to the solution.

a) Coating the Surface of a Cuvette with CACMAK The surface of a cuvette was coated by leaving on the surface over night (ON) at room temperature (RT) 200 µl mouse IgGl, monoclonal antibody Acl-20.4-2. (CACMAK; Progen Biotechnik GmbH, Heidelberg, Germany) 5 µg/ml in PBS+(PBS+=100 mM $PO_4$, pH 7.5; 100 mM NaCl). Then the surface was washed four times with PBS (phosphate buffered saline) and treated with 1% BSA (bovine serum albumin) Miles Enhanced, PBS+300 µl, for one hour at RT.

b) Placing the Protein Being Assayed in Contact with the Surface GAMAPC (a conjugate of allphycocyanin (APC) and crosslinked goat anti-mouse IgG (H+L); Molecular Probes, Leiden, Netherlands) in PBS+T (PBS+T=100 mM $PO_4$, pH (7.5; 100 mM NaCl, 0.025 v/v Tween 20) was left on the surface over night at RT. Then, it was washed five times with PBS, and 200 µl PBS-T was added, and the fluorescence was measured by the evanescence field method. The results are shown in Table 1.

TABLE 1

| Concentration of coating solution of antigen CACMAK [µg/µl] | Concentration of GAMAPC [µg/µl] | Emission [photon counts/s] |
|---|---|---|
| 0 | 10 | 3,000 |
| 5 | 10 | 120,000 |
| 5 | 3 | 60,000 |
| 5 | 1 | 18,000 |
| 5 | 0 | 3,000 |

The emission of photons dependent on the concentration of the fluorophor APC bonded to the surface was then found.

EXAMPLE 2

End-point reaction with chip washing and fluorescence measurement. Only bonded fluorophor is present for the measurement.

a) Coating the Surface of a Cuvette The surface of cuvettes was coated by leaving 200 µl of human serum 1:1000 in PBS+ at room temperature (RT) over night on the surface. Then the surface was washed four times with PBS and treated with 1% BSA (bovine serum albumin) Miles enhanced, PBS+, 300 µl for one hour at RT.

b) Placing the Protein Being Assayed in Contact with the Surface Anti-human-IgG-Cy5 conjugate (Amersham Pharmacia Biotech, Dübendorf, Swtizerland) in PBS+T was left on the surface over night at RT. Then, it was washed five times with PBS, and 200 µl PBS+T was added and the fluorescence was measured. The results are shown in Table 2.

TABLE 2

| Coated human serum antigen | Anti-human IgG-Cy5 conjugate | Emission [photon counts/s] |
|---|---|---|
| 0 | 1:100 | 3,000 |
| 1:1000 | 1:100 | 7,000 |
| 1:1000 | 1:300 | 6,000 |
| 1:1000 | 1:1000 | 5,000 |
| 1:1000 | 0 | 3,000 |

In turn, it was possible to measure the emission of photons dependent on the concentration of the bonded fluorophor Cy5.

EXAMPLE 3

In this example, the effectiveness of different dyes in reducing volume absorption is studied. The surface of the cuvette was not coated in this example, and only the reduction in fluorescence of the conjugate of protein and fluorophor in the solution was determined. The fluorophors in the volume of the reaction solution were excited by small amounts of scatter light fluoresced. The absorption spectra of the dyes used are shown in FIG. 5.

GAMAPC 10 µg/ml in PBS+T is mixed with different dyes and the fluorescence is measured by volume excitation. The results are shown in Table 3.

TABLE 3

| Dye Added | Absorption of Dye at 650 nm | Emission of Fluorophor [fluorescence counts/s] |
|---|---|---|
| Cuvette without fluorophor | — | 3,300 |
| No absorber dye | 0.00 | 210,000 |
| Brilliant Blue FCF[1] 0.25 mM | 0.55 | 4,200 |
| Amaranth[2] 1 mM | 0.05 | 120,000 |
| 5% Supercook Blue[3] | 0.30 | 4,400 |
| 5% Supercook Green[3] | 0.10 | 23,000 |
| 5% Supercook Egg Yellow[3] | <0.04 | 190,000 |
| 5% Supercook Pink[3] | <0.04 | 200,000 |
| 5% Supercook Cochineal[3] | 0.05 | 99,000 |

Notes:
[1]Brilliant Blue FCF (Erioglaucine A), Fluka, Buchs, Switzerland
[2]Amaranth, Fluka, Buchs, Switzerland
[3]Supercook Food Colourings, Supercook, Leeds, Great Britain It was thus found that when APC was used as fluorophor, dyes or mixtures of them that absorb between 600 and 700 nm reduce the volume fluorescence by absorption of the light that shines in and/or is emitted.

EXAMPLE 4

In this example, the dependence of reducing volume fluorescence on the concentration of the dye Brilliant Blue FCF using APC as a fluorophor is studied.

a) Preparation of Cuvette The cuvette is blocked with 1% BSA Miles enhanced, in PBS+300 µl for one hour at RT.

b) Placing the Solution Containing the Fluorophor and the Dye in Contact GAMAPC (10 µg/ml) in PBS+T is mixed with Brilliant Blue FCF in different concentrations, and the fluorescence of the volume excitation is measured.

TABLE 4

| Dye in PBS + T added | Concentration of dye [mM] | Emission of fluorophor [fluorescence counts/s] |
|---|---|---|
| None (only cuvette) | — | 3,300 |
| None (cuvette + GAMAPC) | — | 106,000 |
| GAMAPC + Brilliant Blue FCF[4] | 0.02 | 26,000 |
| GAMAPC + Brilliant Blue FCF[4] | 0.04 | 9,000 |
| GAMAPC + Brilliant Blue FCF[4] | 0.08 | 4,000 |
| GAMAPC + Brilliant Blue FCF[4] | 0.16 | 4,000 |
| GAMAPC + Brilliant Blue FCF[4] | 0.32 | 4,000 |
| GAMAPC + Brilliant Blue FCF[4] | 0.63 | 4,000 |
| GAMAPC + Brilliant Blue FCF[4] | 1.25 | 4,000 |
| GAMAPC + Brilliant Blue FCF[4] | 2.50 | 4,000 |
| GAMAPC + Brilliant Blue FCF[4] | 5.0 | 4,000 |
| GAMAPC + Brilliant Blue FCF[4] | 10.0 | 4,000 |

Note:
[4]Brilliant Blue FCF (Erioglaucine A), Fluka, Buchs, Switzerland.

The reduction in volume excitation depends on the concentration of Brilliant Blue dye in the volume. With Brilliant Blue FCF, at a concentration of only 0.04 mm and above, far more than 95% of the volume fluorescence is suppressed.

EXAMPLE 5

In this example, the influence of the dye on the fluorescence of the fluorophor bonded to the surface is studied. End-point reaction with surface washing and fluorescence measurement. Only bonded fluorophor is measured.

A cuvette prepared as in Example 1a) is placed in contact with GAMAPC in PBS+T over night at RT and then washed five times with PBS.

After 200 µl of PBS+T is added, mixed with Brilliant blue FCF in different concentrations, the fluorescence of GAMAPC 10 µg/ml in PBS+T bonded to the surface of the cuvette and the fluorescence was measured by volume excitation.

TABLE 5

| Dye in PBS + T added | Concentration of dye [mM] | Emission of fluorophor [fluorescence counts/s] |
|---|---|---|
| None (only cuvette) | — | 3,300 |
| None (cuvette + GAMAPC) | — | 126,000 |
| GAMAPC(bonded) + Brilliant Blue FCF[5] | 0.02 | 115,000 |
| GAMAPC(bonded) + Brilliant Blue FCF[5] | 0.04 | 94,000 |
| GAMAPC(bonded) + Brilliant Blue FCF[5] | 0.08 | 74,000 |
| GAMAPC(bonded) + Brilliant Blue FCF[5] | 0.16 | 56,000 |
| GAMAPC(bonded) + Brilliant Blue FCF[5] | 0.32 | 42,000 |
| GAMAPC(bonded) + Brilliant Blue FCF[5] | 0.63 | 29,000 |
| GAMAPC(bonded) + Brilliant Blue FCF[5] | 1.25 | 19,000 |
| GAMAPC(bonded) + Brilliant Blue FCF[5] | 2.50 | 12,000 |
| GAMAPC(bonded) + Brilliant Blue FCF[5] | 5.0 | 9,000 |
| GAMAPC(bonded) + Brilliant Blue FCF[5] | 10.0 | 8,000 |

Note:
[5]Brilliant Blue FCF (Erioglaucine A), Fluka, Buchs, Switzerland.
A reduction in evanescence field excitation of the bonded APC that depended on the concentration of the dye in the volume was found. With a concentration of Brilliant Blue of 0.04 mM, roughly 35% of the bonded fluorescence is suppressed, i.e., the reduction in bonded fluorescence is much smaller than the reduction in fluorescence by volume excitation, where more than 95% of the fluorescence was suppressed by adding dye in the same concentration.

EXAMPLE 6

This example shows that the emission of fluorophors, which are bonded to the surface, is not inhibited much by the amount of dye added, while the volume excitation is sharply reduced. The result is a better signal/noise ratio and hence lower detection limits. A cuvette prepared as in Example 1a) is placed in contact with GAMAPC in PBS+T over night at RT and then washed five times with PBS. Then, as in Example 1b), GAMAPC in PBS+T was left over night at RT on the surface. Then, it was washed five times with PBS.

The cuvettes prepared in this way went through the following different fluorescence measurements:
(1) After PBS+T was added (only bonded fluorophor)
(2) After APC was added (10 µg/ml in PBS+T) (bonded fluorophor+fluorophor in volume, but without dye)
(3) After APC 10 µg/ml and Brilliant Blue FCF (BB FCF) (0.25 mM in PBS+T) (bonded fluorophor+fluorophor in volume+dye) are added

TABLE 6

| | | | Emission [Fluorescence Count/s] | | |
|---|---|---|---|---|---|
| Chip | Mab µg/ml | GAMAPC µg/ml | (1) PBS + T | (2) PBS + T APC 10 µg/ml | (3) PBS + T APC 10 µg/ml BB FCF 0.25 mM |
| M1 | 0 | 10 | 3,000 | 230,000 | 5,000 |
| M2 | 5 | 10 | 120,000 | 300,000 | 59,000 |
| M3 | 5 | 3 | 72,000 | 280,000 | 29,000 |
| M4 | 5 | 1 | 26,000 | 170,000 | 16,000 |
| M5 | 5 | 0.3 | 5,500 | 230,000 | 7,200 |
| M6 | 5 | 0.1 | 4,600 | 230,000 | 6,000 |

TABLE 7

| | Signal/noise Ratio[6] | |
|---|---|---|
| Chip | (2) without Brilliant Blue FCF | (3) with Brilliant Blue FCF |
| M1[7] | — | — |
| M2 | 1.3 | 11.8 |
| M3 | 1.2 | 5.8 |
| M4 | 0.7 | 5.8 |
| M5 | 1.0 | 3.2 |
| M5 | 1.0 | 1.2 |

Notes:
[6]Signal/noise ratio = ratio of surface emissions ("signal") to volume emissions ("noise")
[7]Noise = Chip M1 - negative reaction (negative control).

Results:
1. Decreasing concentration series GAMAPC from M2 to M6. The negative control M1 has an emission of 3,000 counts/s.
2. Without the addition of a dye, i.e., with APC excitation in the volume not suppressed, no clear decreasing concentration series can be seen from M2 to M6. Above all, small values disappear in the background of the volume excitation.
3. With Brilliant Blue FCF in the volume, the decreasing series of concentrations, M2 to M6, can be clearly seen. The negative control M1 has 5,000 counts/s. Due to Brilliant Blue FCF, the emission of the volume by APC is reduced from 230,000 counts/s M1 to 5,000 counts/s.

The specific surface-bonded fluorescence is reduced by roughly 50%. The signal/noise ratio is much improved by the addition of Brilliant Blue FCF.

EXAMPLE 7

This example measured the reaction kinetics of absorption of a fluorophor-marked protein on a reaction partner bonded to the surface of the cuvette.

In a cuvette prepared as in Example 1a), GAMAPC in PBS+T was added, and the fluorescence was measured depending on the time.

Figure 7:
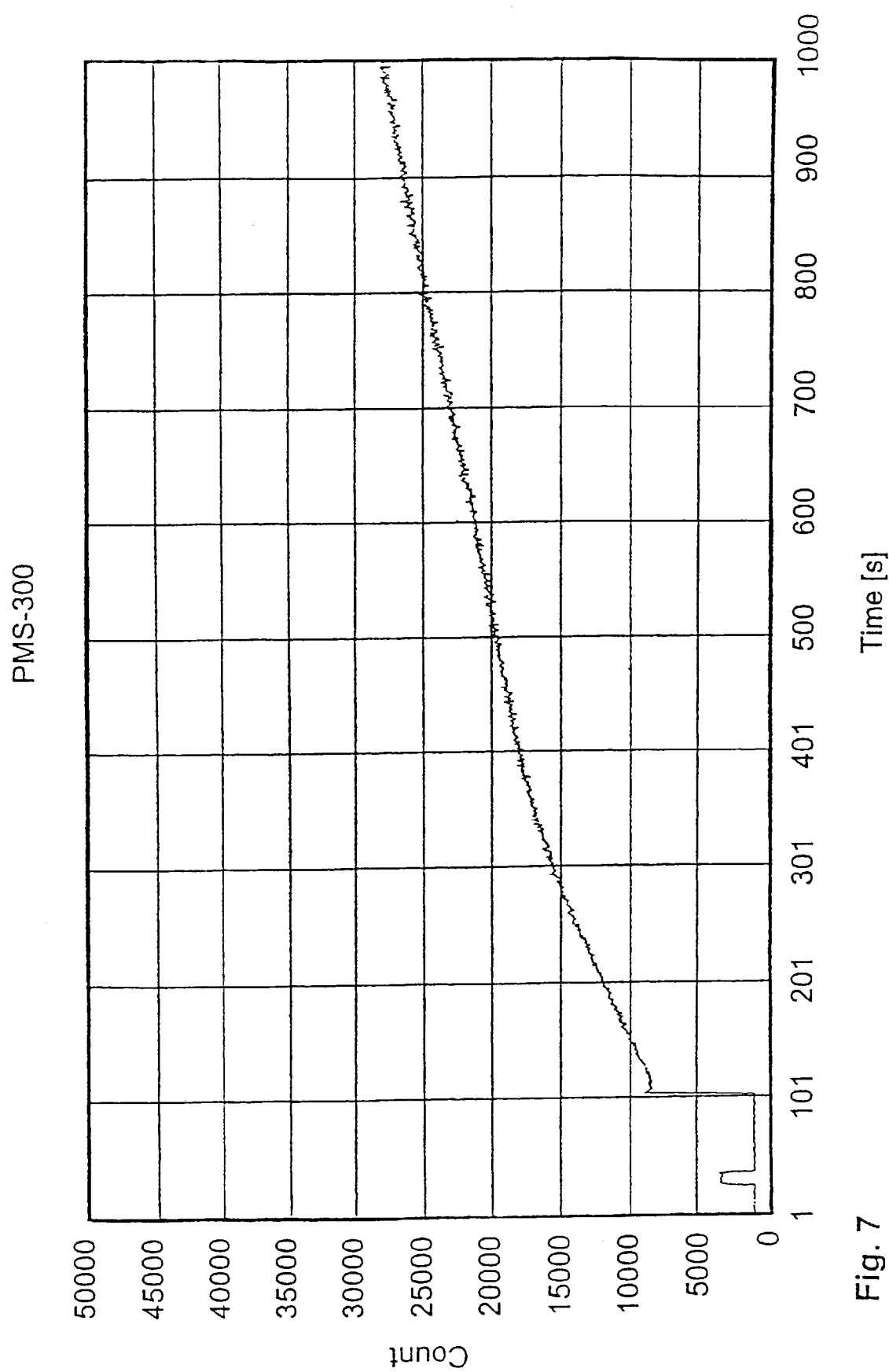
FIG. 7 shows a reaction kinetic measured by the method in the invention for the absorption of a protein on reaction partner R1 bonded to the surface.

FIG. 7 shows the change in emission against the time. The addition of GAMAPC was at T=100 s. An increase in emission (fluorescence count) was observed with the reaction time, which corresponded to the absorption of the fluorophor-marked protein on the reaction partner bonded to the surface.

Figure 8:
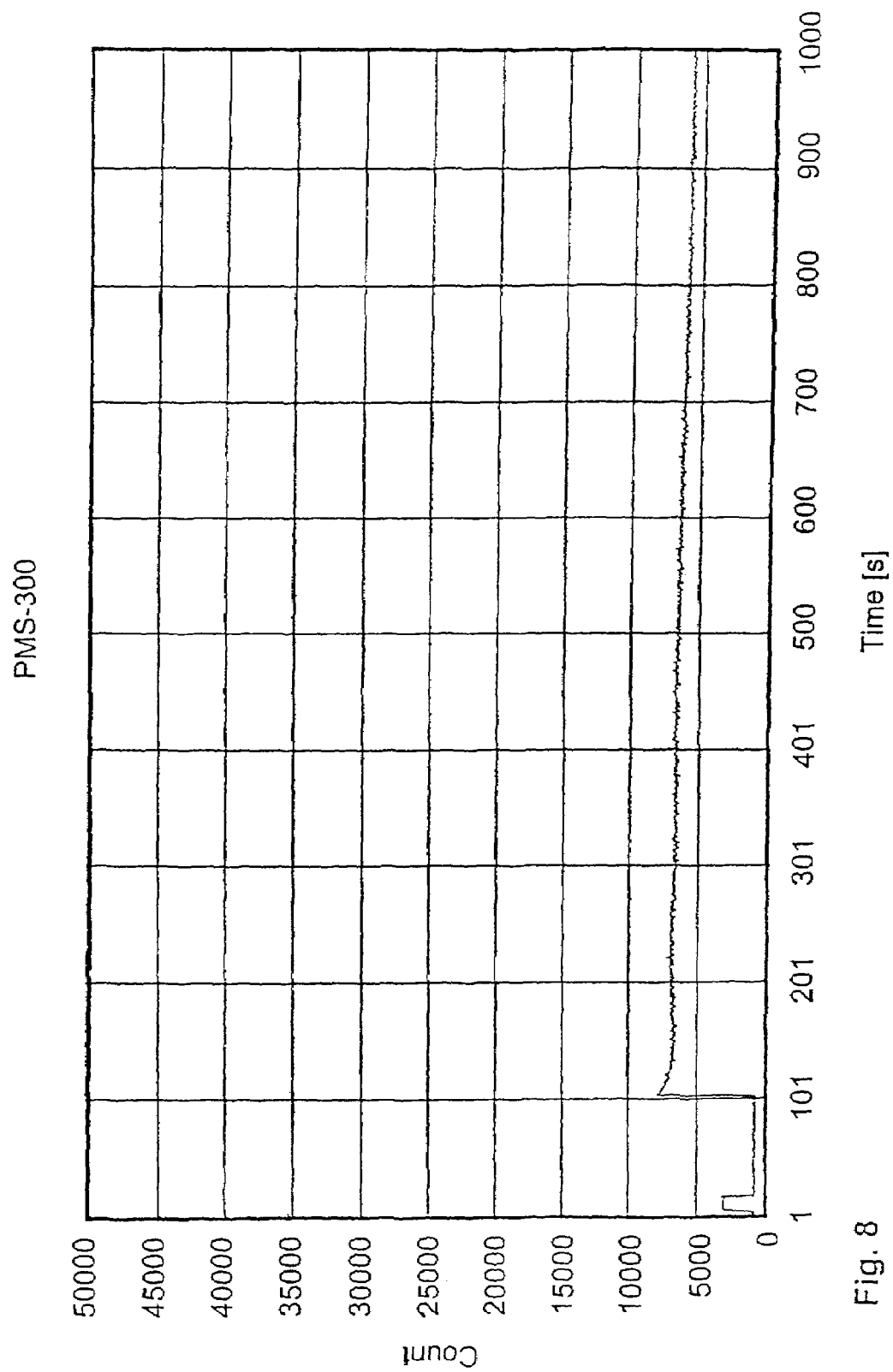
FIG. 8 shows a comparative measurement for the reaction kinetics in FIG. 7 measured in FIG. 7.

For comparison, the change in emission with time was measured on a sample, in which the surface of the cuvette was not coated with mouse-1gG as in Example 1a (See FIG. 8). The emission did not increase with time, but remained stable.

The invention claimed is:

1. A method of assaying substances comprising the steps:
providing a surface that has a top and a bottom and at least one reaction partner R1 bonded to the top of said surface;
placing in contact with said surface a solution that contains at least the substance being assayed, at least one compound containing a fluorophor and at least one dye that absorbs in the absorption and/or emission range of the fluorophor, wherein a complex forms on reaction partner R1 on said surface and wherein said complex is formed by covalent or non-covalent interactions of reaction partner R1 with the substance being assayed and by covalent or non-covalent interactions of the at least one compound containing a fluorophor with the substance being assayed;
projecting a beam of light onto the bottom of the surface, said beam of light being totally reflected on the surface of the phase boundary, thereby forming an evanescence field over said surface, wherein said dye is present in the solution at a concentration sufficient to absorb 70% or more of the light entering the solution within 1 mm above the top of said surface; and
exciting the fluorophor bonded to said surface by said evanescence field and measuring the fluorescence produced as a measure of the substance being assayed.

2. The method according to claim 1, wherein the substance being assayed, bonds to reaction partner R1 on said surface as reaction partner R2.

3. The method according to claim 2, wherein the reaction partner R1 bonded to said surface is an antigen or an antibody.

4. The method according to claim 1, wherein a reaction partner R2 contains the substance being assayed and bonds to reaction partner R1 on said surface along with said substance being assayed.

5. The method according to claim 1, wherein another compound, which contains a bonding site for the substance being assayed and a reaction partner R2, bonds to reaction partner R1 on the surface.

6. The method according to claim 5, wherein reaction partner R1 includes avidin or streptavidin and reaction partner R2 includes biotin and a binding site for the substance being assayed.

7. The method according to claim 1, wherein the substance being assayed includes a biologically active substance, which is selected from the group consisting of hormones, proteins, viruses, bacteria, pharmaceuticals and toxins.

8. The method according to claim 7, wherein:
the substance being assayed is a protein;
the compound containing fluorophor further contains a binding site for the substance being assayed;
fluorescing proteins and/or low-molecular weight fluorescing chemical compounds are used as the fluorophor;
phycobili proteins are used as fluorescing proteins;
a mixture of dyes that absorb in the absorption and/or emission range of the fluorophor is used; and
at least one dye that absorbs in a wavelength range from 600 to 700 nm is used.

9. The method according to claim 8, further comprising the steps of determining reaction kinetics of immunologic reactions.

10. The method according to claim 8, further comprising the steps of carrying out an assay selected from the group consisting of medical or veterinary medical diagnostics, food analysis, environmental analysis or analysis of fermentation processes.

11. The method according to claim 8, wherein the protein is an antigen or an antibody.

12. The method according to claim 8, wherein the phycobili proteins are selected from the group consisting of allophycocyanine (APC) and low-molecular weight cryptomonad-derived phycobili proteins.

13. The method according to claim 8, wherein Cy5 or BODIPY are used as low-molecular weight fluorescing compounds.

14. The method according to claim 8, wherein a fluorophor that absorbs in a wavelength range from 600 to 700 nm is used.

15. The method according to claim 8, wherein at least one phosphorescing compound is used as the fluorophor.

16. The method according to claim 1, wherein the substance being assayed is a protein.

17. The method according to claim 16, wherein the protein is an antigen or an antibody.

18. The method according to claim 1, wherein the compound containing a fluorophor further contains a binding site for the substance being assayed.

19. The method according to claim 1, wherein fluorescing proteins and/or low-molecular weight fluorescing chemical compounds are used as the fluorophor.

20. The method according of claim 19, wherein phycobili proteins are used as fluorescing proteins.

21. The method according to claim 20, wherein 5-N-N'-diethyltetramethylindodicarbocyanine (Cy5) or dipyrromethene boron difluoride (BODIPY) are used as low-molecular weight fluorescing compounds.

22. The method according to claim 20, wherein the phycobili proteins are selected from the group consisting of allophycocyanine (APC) and low-molecular weight cryptomonad-derived phycobili proteins.

23. The method according to claim 1, wherein at least one fluorophor that absorbs in a wavelength range from 600 to 700 nm is used.

24. The method according to claim 1, wherein at least one phosphorescing compound is used as the fluorophor.

25. The method according to claim 1, wherein a mixture of dyes that absorb in the absorption and/or emission range of the fluorophor is used.

26. The method according to claim 1, wherein at least one dye that absorbs in a wavelength range from 600 to 700 nm is used.

27. The method according to claim 26, wherein disodium alpha-(4-(N-ethyl-3-sulfonatobenzylamino)phenyl)-alpha-(4-N-ethyl-3-sulfonatobenzylamino, cyclohexa-2,5-dienylidene) toluene-2-sulfonate (Brilliant Blue FCF) in a concentration of at least 0.001 mM is used as the at least one dye.

28. The method according to claim 1, further comprising the step of determining reaction kinetics of immunologic reactions.

29. The method according to claim 1, further comprising the step of carrying out an assay selected from the group consisting of medical or veterinary medical diagnostics, food analysis, environmental analysis or analysis of fermentation processes.

* * * * *

UNITED STATES PATENT AND TRADEMARK OFFICE
CERTIFICATE OF CORRECTION

| | | |
|---|---|---|
| PATENT NO. | : 7,205,155 B1 | Page 1 of 1 |
| APPLICATION NO. | : 10/049975 | |
| DATED | : April 17, 2007 | |
| INVENTOR(S) | : Manfred Schawaller et al. | |

It is certified that error appears in the above-identified patent and that said Letters Patent is hereby corrected as shown below:

Column 3, Line 13, "component" should read --compound--.

Column 3, Line 28, "Walls interactions" should read --Waals interaction--.

Column 4, Line 15, "can an" should read --can have an--.

Column 6, Line 62, "signal to" should read --signal is--.

Column 7, Line 60, "are blends" should read --or blends--.

Column 9, Line 8, "pH (7.5;" should read --pH 7.5;--.

Column 9, Line 43, "Swtizerland" should read --Switzerland--.

Signed and Sealed this

Fifth Day of August, 2008

JON W. DUDAS
*Director of the United States Patent and Trademark Office*